United States Patent [19]

Takagi et al.

[11] 4,378,803

[45] Apr. 5, 1983

[54] PROCESS FOR PRODUCING ANTITHROMBOGENIC VINYL ACETATE POLYMER OR HYDROLYZATE THEREOF

[75] Inventors: Kunihiko Takagi, Kyoto; Yasunori Yabushita, Yamatotakada, both of Japan

[73] Assignee: Unitika, Ltd., Hyogo, Japan

[21] Appl. No.: 209,360

[22] Filed: Nov. 24, 1980

Related U.S. Application Data

[63] Continuation of Ser. No. 43,601, May 29, 1979, abandoned.

[30] Foreign Application Priority Data

May 27, 1978 [JP] Japan .................................. 53-63660

[51] Int. Cl.³ .................... A61M 25/00; C08F 8/30; C08F 8/32
[52] U.S. Cl. .................................. 604/280; 3/1; 424/33; 424/78; 435/180; 435/181; 523/112; 524/21; 525/61
[58] Field of Search ...................... 260/8; 424/78, 33; 435/180, 181; 128/349 R, 350 R, 348; 523/112; 524/21; 525/61

[56] References Cited

U.S. PATENT DOCUMENTS

| | | | |
|---|---|---|---|
| 3,616,229 | 10/1971 | Wildi et al. | 424/78 |
| 3,625,745 | 12/1971 | Wright et al. | 424/31 |
| 3,625,827 | 12/1971 | Wildi et al. | 435/181 |
| 3,673,612 | 7/1972 | Merrill et al. | 424/82 |
| 4,055,635 | 10/1977 | Green et al. | 424/78 |
| 4,273,873 | 6/1981 | Sugitachi et al. | 424/78 |
| 4,307,151 | 12/1981 | Yamauchi et al. | 435/180 |

OTHER PUBLICATIONS

Immobilized Enzymes, Zaborsky, CRC Press, (1973), pp. 146–147.
CA, 86, 161349(m), (1977).

*Primary Examiner*—Stanford M. Levin
*Attorney, Agent, or Firm*—Sughrue, Mion, Zinn, Macpeak and Seas

[57] ABSTRACT

A process for producing an antithrombogenic vinyl acetate polymer or a hydrolyzate thereof which comprises treating the vinyl acetate polymer or hydrolyzate with a solution of a fibrinolytic enzyme so as to fix the fibrinolytic enzyme to the polymer. The resulting antithrombogenic vinyl acetate polymer or hydrolyzate is advantageously used in a material which comes into contact with the blood in use and is especially useful in a surgical tube.

29 Claims, No Drawings

PROCESS FOR PRODUCING ANTITHROMBOGENIC VINYL ACETATE POLYMER OR HYDROLYZATE THEREOF

This is a continuation of application Ser. No. 43,601, filed May 29, 1979, now abandoned.

BACKGROUND OF THE INVENTION

1. Field of the Invention

This invention relates to a process for producing an antithrombogenic vinyl acetate polymer or hydrolyzate.

2. Description of the Prior Art

A material obtained by fixing urokinase to the surface of a nylon tube is described in A. Sugitachi, K. Takagi, *The International Journal of Artificial Organs*, Vol. 1, No. 2, pp. 88–92 (1978) as having superior antithrombogenic properties and as being suitable for clinical applications such as in the form of surgical drains, intravenous catheters, etc. Sugitachi et al, supra, state that the nylon tube is somewhat non-elastic for clinical applications and to remedy this defect urokinase was fixed to a silicone tube which is softer but does not have as good antithrombogenic property.

The inventors of the present application have previously developed a process for preparing an elastic antithrombogenic material by fixing a fibrinolytic substance to a polyester elastomer, e.g., as disclosed in Japanese patent application (OPI) No. 113194/78 (the term "OPI" as used herein refers to a "published unexamined Japanese patent application"). However, the resulting elastic antithrombogenic material is opaque, has a lower creep resistance than silicone, and is unable to accommodate a large volume of contrast media for X-ray photography such as barium sulfate which is detrimental to its softness.

Two U.S. patent applications are now pending filed in the names of the present inventors. One is entitled "A Process for Producing an Antithrombogenic Material by Fixation of a Synthesized Fibrinolytic Compound", Ser. No. 844,856, filed Oct. 25, 1977, U.S. Pat. No. 4,273,873 and the other is "A Process for Producing an Antithrombogenic Polyurethane by Fixation of a Fibrinolytic Enzyme to the Surface of Polyurethane", Ser. No. 928,496, filed July 27, 1978, now abandoned.

SUMMARY OF THE INVENTION

It is a primary object of this invention to provide an antithrombogenic material suitable for use in clinical applications which is flexible, transparent, and X-ray opaque.

The present invention provides a process for producing an antithrombogenic vinyl acetate polymer or hydrolyzate by treating a vinyl acetate polymer or hydrolyzate with a solution of fibrinolytic enzyme so as to fix the fibrinolytic enzyme to the polymer.

DETAILED DESCRIPTION OF THE INVENTION

The term "vinyl acetate polymer" as used herein includes both homopolymers and copolymers of vinyl acetate. Examples of the suitable comonomers are ethylenically unsaturated compounds such as vinyl esters such as vinyl formate, vinyl propionate, vinyl benzoate, and vinyl stearate; olefinic hydrocarbons such as ethylene and propylene; chlorinated olefins such as vinyl chloride and vinylidene chloride; acrylic monomers such as methyl methacrylate, ethyl acrylate, and $\beta$-hydroxyethyl methacrylate; allyl derivatives such as allyl alcohol and N-allyl urethane; and $\alpha,\beta$-unsaturated acid anhydrides such as maleic anhydride and itaconic anhydride. The vinyl acetate copolymer having these monomeric components may be a random copolymer, an alternating copolymer, a block copolymer or a graft copolymer.

The vinyl acetate polymer is prepared by bulk, solution, emulsion or suspension polymerization of the corresponding vinyl monomers in the presence of a free radical initiator. Examples of suitable free radical initiators are peroxides such as benzoyl peroxide, lauroyl peroxide, acetyl peroxide, t-butylhydroperoxide, etc.; azo-compounds such as azobisisobutyronitrile; and redox initiators such as t-butyl perbenzoate-ascorbic acid. A suitable amount for the initiator ranges from about 0.0001 to about 5 wt%, preferably from 0.001 to 2 wt%, based on the vinyl monomer. A suitable polymerization temperature ranges from about $-50°$ to about 250° C., preferably from about 10° to 180° C. A suitable polymerization time is from about 1 minute to 100 hours, preferably from about 5 minutes to 50 hours.

The vinyl acetate polymer is shaped into a tube, film, sheet, elastomer, fiber and other desired forms depending upon its use. Alternatively, the polymer is coated on the surface of a shaped article made of another material. A filler such as a fiber, non-woven cloth and glass fiber can optionally be incorporated into the vinyl acetate polymer in the course of its shaping in an amount ranging from about 0.1 to about 50 wt% of the polymer. For the production and shaping of the vinyl acetate polymer, reference may be had to "Vinyl Ester Polymers", *Encyclopedia of Polymer Science and Technology*, Vol. 15, p. 531, Interscience Publishers (1971) and *Polyvinyl Alcohol*, edited by C. A. Finch, John Wiley & Sons (1973).

The vinyl acetate polymer may be converted to the corresponding vinyl alcohol polymer by alkaline hydrolysis, ammonolysis or acid hydrolysis. Alkaline hydrolysis is most commonly used on an industrial scale. Alkaline hydrolysis of the vinyl acetate polymer is performed in methanol, ethanol, water or a mixture thereof containing from about 0.1 to about 10 N, preferably 0.5 to 6 N, of an alkali such as sodium hydroxide, potassium hydroxide or sodium methoxide at a temperature ranging from about 10° C. to the boiling point of the solvent for a period of time ranging from about 0.5 minute to about 48 hours, preferably from 1 minute to 24 hours. By controlling the conditions under which the vinyl acetate polymer is hydrolyzed, hydrolyzates of the polymer can be produced in varying degrees of hydrolysis. Antithrombogenic articles may be prepared from the hydrolyzate or the surface of and article such as a tube, sheet, film, etc., into which the vinyl acetate polymer has been shaped may be hydrolyzed. When the vinyl acetate polymer is hydrolyzed under a homogeneous or suspended condition before shaping from the standpoint of preparing a uniform hydrolysis product, the hydrolysis degree is at least about 50% and preferably about 60% or more. For hydrolysis and shaping of the vinyl acetate polymer, reference may be made to "Vinyl Alcohol Polymers", *Encyclopedia of Polymer Science and Technology*, Vol. 14, p. 149, Interscience Publishers (1971), and *Polyvinyl Alcohol*, supra.

A surgical drain, catheter and other medical tubes are preferably prepared from a copolymer of ethylene and vinyl acetate. An ethylene-vinyl acetate copolymer may be prepared by copolymerizing ethylene and vinyl acetate as described in U.S. Pat. Nos. 2,395,381, and 2,703,794, and British Pat. Nos. 569,927, 835,466, 875,983, 807,112, 843,974 and 929,138. The ethylene-vinyl acetate copolymer exhibits different properties depending upon the vinyl acetate content. Since an antithrombogenic material for use in clinical applications should be flexible and strong at the same time, the vinyl acetate content is preferably about 3 to 45 wt%, more preferably about 5 to 40 wt%, of the polymer. If the vinyl acetate content does not reach 3 wt%, flexibility is impaired, and if it exceeds 40 wt%, toughness is compromised.

An antithrombogenic material for use in clinical applications is preferably prepared from the ethylene-vinyl acetate copolymer for the following advantages: (i) because the copolymer is thermoplastic, the copolymer is adaptable for extrusion molding; (ii) it has high transparency; (iii) the polymer is particularly advantageous as a surgical drain or intravenous catheter because flexibility is achieved without a plasticizer; (iv) the polymer is highly stable during molding procedure which not only eliminates the chance of including a decomposition product harmful to the resulting shaped article but also obviates the need of adding an injurious heat stabilizer; (v) the polymer which possesses good adhesion is obtained in a molten state, which proves particularly advantageous in preparing a shaped article of intricate form; and (vi) the polymer is able to accommodate filler loadings without experiencing a significant change in its physical properties, that is, a medical tube made of the polymer does not lose its flexibility even if it is filled with a high concentration of a contrast medium such as barium sulfate when the X-ray opacity mark is placed in the medical tube.

The fibrinolytic enzymes used in this invention take part in the dissolution of fibrin. Examples of the suitable fibrinolytic enzyme are proteases useful as native enzymes such as urokinase, streptokinase, plasmin and brinolase. Urokinase extracted from human urine is advantageously used in view of effectiveness and safety.

These fibrinolytic enzymes are fixed to the surface of the vinyl acetate polymer or hydrolyzate thereof by means of covalent bonding or adsorption. For the vinyl acetate polymer or its hydrolyzate to exhibits its antithrombogeneity over an extended period of time the fibrinolytic enzyme is desirably fixed by covalent bonding. However, fixation by adsorption serves the purpose of providing a polymer or hydrolyzate which is effective for a short period of time.

One method of fixing a fibrinolytic enzyme by covalent bonding is by treating the surface of a vinyl acetate polymer or hydrolyzed vinyl acetate polymer containing a reactive functional group capable of forming a covalent bond with a solution of the enzyme. O. Zaborsky, *Immobilized Enzymes*, CRC Press (1973) describes a number of reactive functional groups which are capable of forming a covalent bond by reacting with an amino group, a carboxyl group, a sulfhydryl group, an imidazole group or the phenol group present in a fibrinolytic enzyme. Of these functional groups, isocyanate, epoxy, formyl, acid chloride, carboxylic acid anhydride, amino, carboxyl, azide and diazo groups are easily used for the purpose of this invention. These functional groups should be incorporated into the polymer in amounts such that the amount of the fibrinolytic enzyme immobilized provides a thrombus formation time of about 45 minutes or more.

A vinyl acetate polymer or hydrolyzate thereof containing these reactive functional groups may be prepared by copolymerizing vinyl acetate with a comonomer containing a reactive functional groups. Suitable comonomers include acrolein (to introduce a formyl group), itaconic anhydride (to introduce an acid anhydride group), methacrylic acid (to introduce a carboxyl group). The most suitable comonomer is maleic anhydride; examples of the vinyl acetate copolymer having maleic anhydride as a copolymerizable component are a vinyl acetate-maleic anhydride copolymer and a vinyl acetate-maleic anhydride-vinyl chloride terpolymer. These copolymers can be prepared by reference to the methods disclosed in British Pat. No. 844,509 and U.S. Pat. Nos. 2,483,465 and 3,010,846. A suitable copolymerization amount for maleic anhydride is about 0.1 to 70 mol%, preferably 0.5 to 60 mol%.

Another method of producing a vinyl acetate polymer or its hydrolyzate having the above mentioned reactive functional groups is to hydrolyze the polymer first and then introduce the reactive functional groups into the hydrolyzate.

An isocyanate group may be introduced into the hydrolyzate of vinyl acetate polymer by first dissolving a polyisocyanate such as hexamethylene diisocyanate, 4,4'-diphenylmethane diisocyanate, toluene diisocyanate, xylene diisocyanate or phenylene diisocyanate in a solvent composed of dimethylformamide, methyl ethyl ketone, tetrahydrofuran or a mixture thereof to provide a solution at a concentration of about 0.1 to 50 wt%, preferably about 0.5 to 20 wt%. Optionally a catalyst such as N-methyl morpholine or triethylene diamine may be present in an amount of about 0.001 to 10 wt%, preferably about 0.01 to 1 wt%. The resulting solution is then used to treat the hydrolyzate of the vinyl acetate polymer at a temperature in the range of from about 20° to 120° C., preferably about 40° to 90° C., for a period of about 5 minutes to 24 hours, preferably about 20 minutes to 10 hours.

An epoxy group may be introduced into the hydrolyzate by reacting the hydrolyzate either with a glycidyl halide such as epichlorohydrin or epibromohydrin or with a polyglycidyl ether of a polyol such as ethylene glycol, tetramethylene glycol, diethylene glycol or glycerin pentaerythritol in the presence of an aqueous solution of alkali such as sodium hydroxide. For detailed information on the conditions for such reaction, reference may be made to J. Porath, N. Fonstedt, *Journal of Chromatography*, 51, p. 479 (1970) and L. Sundberg, J. Porath, *Journal of Chromatography*, 90, p. 87 (1974).

A formyl group may be introduced into the hydrolyzate of a vinyl acetate polymer by first dissolving a polyaldehyde such as glutaraldehyde, glyoxal or dialdehyde starch in an aqueous solution of an acid such as hydrochloric acid, sulfuric acid or acetic acid to provide a solution having a concentration of about 0.1 to 50 wt%, preferably about 0.5 to 20 wt%. The resulting solution is used to treat the hydrolyzate of the vinyl acetate polymer at a temperature ranging from about −20° to about 100° C., preferably from 0° to 80° C., for a period ranging from about 5 minutes to about 24 hours, preferably from 10 minutes to 10 hours.

An acid chloride group may be introduced into the hydrolyzate of a vinyl acetate polymer by first dissolving a polyacid chloride such as adipoyl chloride, terephthaloyl chloride or cyanuric chloride in acetone, tetrahydrofuran, benzene, toluene, dimethylacetamide or a mixture thereof at a concentration of about 0.1 to about 50 wt%, preferably about 0.5 to 20 wt%, and using the resulting solution to treat the hydrolyzate at a temperature in the range of from −20° to about 90° C., preferably about 0° to 70° C., for about 5 minutes to 24 hours, preferably for about 30 minutes to 10 hours.

An acid anhydride group may be introduced into the hydrolyzate of a vinyl acetate polymer by first dissolving a polycarboxylic acid anhydride such as a maleic anhydride/methyl vinyl ether copolymer, maleic anhydride/styrene copolymer or a maleic anhydride/ethylene copolymer in acetone, tetrahydrofuran, benzene, toluene, dimethylformamide, dimethyl sulfoxide or a mixture thereof in a concentration of about 0.1 to 30 wt%, preferably about 0.5 to 10 wt%, optionally in the presence of from about 0.01 to about 10 wt%, preferably from 0.05 to 2 wt%, of a catalyst such as hydrochloric acid, sulfuric acid, acetic acid, etc., and using the resulting solution to treat the hydrolyzate at a temperature of about 0° to 100° C., preferably about 70° to 80° C., for about 10 minutes to about 24 hours, preferably for about 30 minutes to 10 hours.

An amino group may be introduced into the hydrolyzate of a vinyl acetate polymer by first dissolving an amino acetal such as β-aminoacetaldehyde dimethyl acetal or β-aminoacetaldehyde diethyl acetal in from about 0.1 to about 12 N, preferably 0.5 to 10 N, hydrochloric acid or sulfuric acid, and other aqueous acidic solutions to provide a solution having a concentration of about 1 to 20 wt%, preferably about 2 to 10 wt%, and using the resulting solution to treat the hydrolyzate at a temperature of about 0° to about 100° C., preferably about 20° to 80° C., for about 1 to 48 hours, preferably for about 2 to 24 hours.

An amino group may also be introduced into the hydrolyzate of a vinyl acetate polymer by treating it with a polyfunctional reagent which has at least two functional groups capable of reacting with both a hydroxyl group and an amino group, and then treating the same with a polyamine. Examples of the polyfunctional reagent include polyisocyanates such as hexamethylene diisocyanate, xylene diisocyanate and phenylene diisocyanate; polyepoxides such as polyglycidyl ethers of polyols such as tetramethylene glycol, diethylene glycol, glycerine and pentaerythritol; polycarboxylic acid anhydrides such as a maleic anhydride/methyl vinyl ether copolymer, maleic anhydride/styrene copolymer, and a maleic anhydride/ethylene copolymer; polyaldehydes such as glutaraldehyde, glyoxal and dialdehyde starch; and polyacid chlorides such as adipoyl chloride, terephthaloyl chloride and cyanuric chloride. The hydrolyzate of vinyl acetate polymer can be treated with these polyfunctional reagents under the same conditions as used to introduce an isocyanate, an epoxy, a formyl, an acid chloride, or a carboxylic acid anhydride group into the hydrolyzate as already discussed. The hydrolyzate of the vinyl acetate polymer thus-treated with the polyfunctional reagent is then treated with a polyamine such as ethylene diamine, hexamethylene diamine, diethylene triamine, triethylenetetramine, polyvinylamine, polyethyleneimine, polyaminostyrene, polylysine, or poly(p-aminophenyl alanine). The hydrolyzate may be treated with the polyamine per se if the latter is liquid or alternatively with a polyamine dissolved in methanol, ethanol, propanol, dioxane, tetrahydrofuran, water or a mixture thereof at a concentration of at least about 0.1 wt%, preferably about 1 wt%. A suitable temperature for the treatment ranges from about −20° to about 100° C., preferably from about 0° to 90° C. A suitable treatment time is about 10 minutes to 24 hours, preferably about 30 minutes to 5 hours. If the hydrolyzate of vinyl acetate polymer treated with a polyamine contains a formyl group, it may optionally be subjected to reduction using sodium borohydride or other suitable reducing agent.

An isocyanate group, an epoxy group, a carboxylic acid anhydride group, a formyl group and other reactive functional groups capable of reacting with an amino group can be introduced into a hydrolyzate of a vinyl acetate polymer containing an amino group by treating the hydrolyzate with a polyfunctional reagent having at least two such reactive functional groups. Examples of the suitable polyfunctional reagents are polyisocyanates such as hexamethylene diisocyanate, xylene diisocyanate and phenylene diisocyanate; polyepoxides such as polyglycidyl ethers of polyols such as tetramethylene glycol, diethylene glycol, glycerine and pentaerythritol; polycarboxylic acid anhydrides such as a maleic anhydride/methyl vinyl ether copolymer, maleic anhydride/styrene copolymer, and a maleic anhydride/ethylene copolymer; polyaldehydes such as glutaraldehyde, glyoxal, and dialdehyde starch; and polyacid chlorides such as adipoyl chloride, terephthaloyl chloride and cyanuric chloride. The hydrolyzate of the vinyl acetate polymer containing an amino group is treated with a solution of these polyfunctional reagents in a suitable solvent at a concentration ranging from about 0.05 to 30 wt%, preferably from about 0.1 to 10 wt%, at a temperature ranging from about −20° to 80° C., preferably from about 0° to 60° C., for about 1 minute to about 24 hours, preferably for about 5 minutes to 10 hours.

A carboxyl group may be introduced into the hydrolyzate of a vinyl acetate polymer by dissolving α-haloacetic acid such as α-chloroacetic acid, α-bromoacetic acid or α-iodoacetic acid in about 0.1 to about 5 N, preferably about 0.5 to 4 N, aqueous solution of alkali such as sodium hydroxide or potassium hydroxide to provide a solution at a concentration ranging from about 1 to about 50 wt%, preferably from about 2 to 20 wt%, and then using the resulting solution to treat the hydrolyzate at a temperature ranging from about 0° to about 100° C., preferably from about 20° to 80° C., for a period ranging from about 1 to 24 hours, preferably from about 2 to 12 hours.

The hydrolyzate of vinyl acetate polymer into which a carboxyl group has thus been introduced can have an azo or azide group introduced thereinto in accordance with the method described in W. E. Hornby, H. Filippusson, *Biochimica et Biophysica Acta*, 220, p. 343 (1970) by first treating the hydrolyzate with benzidine or hydrazine, then with nitrous acid.

The surface of the vinyl acetate polymer or its hydrolyzate now containing the reactive functional groups is treated with a solution of a fibrinolytic enzyme so as to fix the enzyme to the surface by means of covalent bonding. The fibrinolytic enzyme should be dissolved in water or a mixture of water and methanol, propanol, acetone, tetrahydrofuran, dioxane, dimethyl sulfoxide or dimethylformamide, with water being present in an amount of at least 50 wt%, and the surface of the vinyl acetate polymer or the hydrolyzed vinyl acetate polymer should be treated with the resultant enzyme solution. A suitable temperature for this treatment is from about −20° to about 50° C., preferably from about 0° C. to 30° C., for about 30 minutes to 48 hours, preferably for about 1 hour to 24 hours. In fixing the fibrinolytic enzyme, the pH must be maintained at about 3 to 10, preferably at about 4 to 9. A buffer such as a phosphate buffer or an acetate buffer, an acid such as hydrochloric acid or an alkali such as sodium hydroxide can be used for this purpose. If desired, a protein such as albumin and gelatin, e.g., in an amount of about 10 g/l or less, or a salt such as sodium chloride, e.g., in an amount of about 2 mol/l or less, can be added to the enzyme solution as a stabilizer.

A dehydrating condensation agent such as N,N'-dicyclohexyl carbodiimide, 1-cyclohexyl-3-(2-morpholinoethyl)-carbodiimide-metho-p-toluenesulfonate, 1-ethyl-3-(3-dimethylaminopropyl)carbodiimide hydrochloride, N-cyclohexyl-5-phenylisoxazolium-3'-sulfonate, 6-chloro-1-p-chlorobenzenesulfonyloxybenzotriazole, or diphenylphosphoryl azide may optionally be added to the enzyme solution in a concentration ranging from about 0.5 to about 200 g/l, preferably from 1 to 100 g/l.

Since the fibrinolytic enzyme can be adsorbed on the vinyl acetate polymer or hydrolyzed vinyl acetate polymer, it can also be fixed to the surface of the polymer by means of adsorption. Adsorptive methods can most effectively be used to fix a large volume of fibrinolytic enzyme to a vinyl acetate polymer or hydrolyzate having a cation exchange group such as a carboxyl group, with the adsorbed enzyme retaining its activity for a relatively long period of time.

To prepare an antithrombogenic material, a fibrinolytic enzyme such as urokinase or streptokinase must be fixed to the surface of the vinyl acetate polymer or hydrolyzed vinyl acetate polymer in an amount sufficient to delay formation of a thrombus for at least 45 minutes. For this purpose, the enzymatic activity of the solution of urokinase or streptokinase to be used for the fixing treatment must be from about 20 to about 100,000 international units/ml, preferably from 100 to 5,000 international units/ml and that of plasmin or brinolase must be from about 10 to about 50,000 casein units/ml, preferably from 50 to 2,500 casein units/ml.

In addition to fixing a fibrinolytic enzyme such as urokinase to the surface of the vinyl acetate polymer or hydrolyzed vinyl acetate polymer, a nitrophthaloyl group or other groups which have an affinity for certain substances present in blood which inhibit fibrinolytic enzymes can optionally be introduced into the polymer or its hydrolyzate by adding 3- or 4-nitrophthaloyl anhydride to a polycarboxylic anhydride solution and thereby introducing an acid anhydride group into the polymer. The inhibiting substances are attracted to the nitrophthaloyl group and the more the inhibiting substance bonds to the nitrophthaloyl group, the less the fibrinolytic enzyme is inhibited by the inhibiting substance.

The antithrombogenic vinyl acetate polymer or its hydrolyzate prepared according to the process of this invention has the following advantages that make it suitable for use as a material which comes into contact with the blood during use: (1) Because of its high moldability, it can be shaped into various forms for various clinical applications; (2) The material prepared from the polymer or its hydrolyzate exhibits high antithrombogenaity over an extended period of time.

This invention is now described in greater detail by reference to the following Examples which are given here for illustrative purposes only and are by no means meant to limit the scope of this invention.

In the Examples, fibrinolytic activity was measured using a fibrin plate having a thickness of about 2 mm which was prepared by adding a physiological saline solution of thrombin from human plasma (25 units/ml) to an aqueous solution of human fibrinogen (0.5 g/ml) in a ratio by volume of 0.2:10. A sample was placed on the fibrin plate and allowed to stand at 37° C. for 24 hours and the fibrinolytic activity was evaluated by the extent of dissolution of the fibrin membrane around the sample.

Antithrombogeneity of a sample in film or sheet form was determined in the following manner. 0.05 ml of citrated plasma (serum to which sodium citrate was added) and 0.05 ml of 0.025 M calcium chloride solution were separately added dropwise onto the sample and mixed together. The mixture was spread over the sample and allowed to stand in a wetting box at 37° C. The time required for the fibrin to precipitate was measured as the thrombus formation time.

The antithrombogeneity of a tubular sample was evaluated by measuring the thrombus formation time using the Chandler rotary tube method as disclosed in A. B. Chandler, *Laboratory Investigations*, 7, p. 110 (1958).

EXAMPLE 1

Two films of polyvinyl alcohol (50μ thick), one cut into a circle 5 mm in diameter and the other into a square (3×3 cm), were immersed in a 4 wt% solution of maleic anhydride-methyl vinyl ether copolymer in acetone at 50° C. for a period of 10 hours. The films were then washed with acetone and dried. The films now containing a carboxylic acid anhydride group were left to stand in a physiological saline solution of urokinase (600 units/ml) at 7° C. for 24 hours, then washed with a physiological saline. The circular film thus treated was subjected to measurement of its fibrinolytic activity wherein a circular dissolution zone 17 mm in diameter appeared around the film. The square film was used to measure the thrombus formation time which was more than 45 minutes.

EXAMPLE 2

Two films of polyvinyl alcohol (50μ thick), one cut into a circle (5 mm in diameter) and the other into a square (3×3 cm), were immersed in a dehydrated tetrahydrofuran solution having dissolved therein 5 wt% of 4,4'-diphenylmethane diisocyanate and 0.1 wt% of N-methyl morpholine, respectively, and heated at the boiling point (66° C.) of tetrahydrofuran for a period of 5 hours. The films were then washed with tetrahydrofuran and dried. The films now containing an isocyanate group were left to stand in a 2 wt% aqueous polyethylene-imine solution at 30° C., water washed and dried. The films thus treated to contain an amino group were immersed in a 4 wt% solution of a maleic anhydride-methyl vinyl ether copolymer in acetone at 20° C. for a period of 2 hours, then washed with acetone and dried. The thus obtained films containing a carboxylic acid anhydride group were left to stand in a physiological saline solution of urokinase (600 units/ml) at 7° C. for a period of 24 hours, then washed with a physiological saline. The circular film thus treated was subjected to measurement of its fibrinolytic activity wherein a circular dissolution zone 21 mm diameter appeared around the film. The square film was used to measure the thrombus formation time which was more than 45 minutes.

EXAMPLE 3

The inside of a tube (I.D. 3 mm, O.D. 5 mm) of an ethylene-vinyl acetate copolymer (containing 19 wt% of vinyl acetate) was treated sequentially as follows:

(1) The inside surface of the tube was partially hydrolyzed by circulating through it a solution of 20 wt% sodium hydroxide in 20 vol% water containing methanol at 60° C. for a period of 3 hours, then a solution of 0.1 vol% acetic acid in methanol was circulated to neutralize the sodium hydroxide solution, followed by washing with water;

(2) A formyl group was introduced into the copolymer by circulating through the tube a solution of 5 wt% dialdehyde starch (degree of oxidation: 45%) in 1 N hydrochloric acid at 50° C. for a period of 4 hours, followed by washing with water;

(3) An amino group was introduced into the copolymer by circulating through the tube a 2 wt% aqueous polyethylene-imine solution at 30° C. for a period of 1 hour, followed by washing with water;

(4) The copolymer was reduced by circulating through the tube a 0.05 wt% aqueous sodium borohydride solution at room temperature for a period of 1 hour, then washed with water and dried;

(5) A carboxylic acid anhydride group was introduced into the copolymer by circulating through the tube a 4 wt% solution of a maleic anhydride/methyl vinyl ether copolymer in acetone at 20° C. for a period of 3 hours, washed with acetone and dried;

(6) The tube was filled with a physiological saline solution of urokinase (600 units/ml), left to stand at 7° C. for a period of 4 hours, and washed with a physiological saline.

A circular dissolution zone 14 mm in diameter appeared around a round slice of the tube to which urokinase was fixed by the procedures described above. The thrombus formation time measured on the tube was more than 45 minutes.

EXAMPLE 4

A mixture of 65 g of vinyl chloride, 25 g of vinyl acetate, 10 g of maleic anhydride and 1 g of lauroyl peroxide was polymerized in 150 g of ethyl acetate at 50° C. for a period of 40 hours. The resulting copolymer was isolated through addition of ethanol. A 5 wt% solution of the copolymer in methyl ethyl ketone was sprayed on a circular nylon film (5 mm in diameter and 200μ thick) and dried at 90° C. for 5 hours. The film was then left to stand in a physiological saline solution of urokinase (600 units/ml) at 7° C. for 24 hours, and washed with a physiological saline. A circular dissolution zone 19 mm in diameter appeared around the film to which urokinase was fixed. The thrombus formation time was more than 45 minutes.

EXAMPLE 5

The inside of a tube (I.D. 3 mm, O.D. 5 mm) of an ethylene-vinyl acetate copolymer (containing 19 wt% of vinyl acetate) was treated sequentially as follows:

(1) The inside surface of the tube was partially hydrolyzed by circulating through it a solution of 20 wt% sodium hydroxide in 20 vol% water in methanol at 60° C. for a period of 3 hours, then a solution of 0.1 vol% acetic acid in methanol was circulated to neutralize the sodium hydroxide solution, followed by washing with water;

(2) An amino group was introduced into the copolymer by circulating through the tube a 2 vol% solution of β-aminoaldehyde diethyl acetal in 1 N hydrochloric acid at 55° C. for a period of 24 hours, and washed with, in the order written, water, 0.01 N sodium hydroxide and water;

(3) A physiological saline solution having dissolved therein 600 units/ml of urokinase and 10 mg/ml of 1-cyclohexyl-3-(2-morpholinoethyl)carbodiimide-metho-p-toluenesulfonate was circulated through the tube at 7° C. for a period of 5 hours, and washed with a physiological saline.

A circular dissolution zone 11 mm in diameter appeared around a round slice of the tube to which urokinase was fixed by the procedures described above. The thrombus formation time was more than 45 minutes.

EXAMPLE 6

The procedure of Example 5 was repeated to hydrolyze the surface of a tube of ethylene-vinyl acetate copolymer and introduce an amino group into the copolymer by means of treatment with β-aminoaldehyde diethyl acetal. Acetone having dissolved therein 4 wt% of a maleic anhydride-methyl vinyl ether copolymer and 0.8 wt% of 3-nitrophthalic anhydride was circulated through the tube at 20° C. for a period of 3 hours, washed with acetone and dried. The tube was then filled with a physiological saline solution of urokinase (600 units/ml), left to stand at 7° C. for 24 hours, and washed with physioligical saline.

A circular dissolution zone 16 mm in diameter appeared around a circular cross-section of the tube to which urokinase was fixed by the procedures described above. The thrombus formation time was more than 45 minutes.

COMPARATIVE EXAMPLE

Control films or tubes were prepared as in Examples 1 to 6 without treatment with fibrinolytic enzyme. No dissolution zone appeared. The thrombus formation time for these control films or tubes ranged from 15 to 20 minutes.

While the invention has been described in detail and with reference to specific embodiments thereof, it will be apparent to one skilled in the art that various changes and modifications can be made therein without departing from the spirit and scope thereof.

What is claimed is:

1. A process for producing an antithrombogenic hydrolyzed ethylene-vinyl acetate copolymer containing about 3 to 45 weight % vinyl acetate and about 97 to 55 weight % ethylene which comprises treating a water-insoluble hydrolyzed ethylene-vinyl acetate copolymer containing about 3 to 45 weight % vinyl acetate and about 97 to 55 weight % ethylene in the form of a shaped article with a solution of a fibrinolytic enzyme so as to fix the enzyme to the copolymer wherein the hydrolyzed vinyl acetate copolymer contains a reactive functional group capable of forming a covalent bond with the fibrinolytic enzyme and the enzyme is fixed to the copolymer through covalent bonding, said reactive functional group being selected from the group consisting of (A) an isocyanate group which has been introduced thereinto by treating the hydrolyzed ethylene-vinyl acetate copolymer with a polyisocyanate, (B) an epoxy group which has been introduced thereinto by treating the hydrolyzed ethylene-vinyl acetate copolymer with a polyepoxide, (C) a formyl group which has been introduced thereinto by treating the hydrolyzed ethylene-vinyl acetate copolymer with a polyaldehyde, (D) an acid chloride group which has been introduced thereinto by treating the hydrolyzed ethylene-vinyl acetate copolymer with an acid chloride, (E) a carboxylic acid anhydride group which has been introduced thereinto by treating the hydrolyzed ethylene-vinyl acetate copolymer with a polycarboxylic acid anhydride, (F) an amino group which has been introduced thereinto by treating the hydrolyzed ethylene-vinyl acetate copolymer with an amino acetal, and (G) an amino group which has been introduced thereinto by first treating the hydrolyzed ethylene-vinyl acetate copolymer with a polyfunctional reagent having at least two functional groups capable of reacting with both a hydroxy group and amino group and then treating the copolymer with a polyamine, said polyfunctional reagent being selected from the group consisting of a polyisocyanate, a polyepoxide, a polycarboxylic acid anhydride, a polyaldehyde and a polyacid chloride.

2. The process of claim 1, wherein the fibrinolytic enzyme is urokinase.

3. The process of claim 1, wherein said fibrinolytic enzyme is streptokinase.

4. The process of claim 1, wherein said fibrinolytic enzyme is plasmin.

5. The process of claim 1, wherein said fibrinolytic enzyme is brinolase.

6. The process of claim 1, wherein a functional group having an affinity for substances in the blood which inhibit fibrinolytic enzymes is present in the polymer or hydrolyzate.

7. The process of claim 6, wherein said group is a nitrophthaloyl group.

8. A process for producing an antithrombogenic hydrolyzed ethylene-vinyl acetate copolymer containing about 3 to 45 weight % vinyl acetate and about 97 to 55 weight % ethylene which comprises treating a water-insoluble hydrolyzed ethylene-vinyl acetate copolymer containing about 3 to 45 weight % vinyl acetate and about 97 to 55 weight % ethylene in the form of a shaped article with a solution of a fibrinolytic enzyme so as to fix the enzyme to the copolymer wherein the hydrolyzed ethylene-vinyl acetate copolymer contains a reactive functional group capable of forming a covalent bond with the fibronolytic enzyme and the enzyme is fixed to the polymer through covalent bonding, said reactive functional group being selected from the group consisting of an isocyanate group, an epoxy group, a formyl group, an acid chloride group, a carboxylic acid anhydride group and the reactive functional group having been introduced thereinto by treating the hydrolyzed ethylene-vinyl acetate copolymer having an amino group with a polyfunctional reagent, selected from the group consisting of a polyisocyanate, a polyepoxide, a polyaldehyde, a polyacid chloride and a polycarboxylic acid anhydride, having at least two of the reactive functional groups capable of reacting with an amino group, and the fibrinolytic enzyme is fixed to the polymer through covalent bonding, wherein said amino group has been introduced:

(A) by treating the hydrolyzed ethylene-vinyl acetate copolymer with an amino acetal; or (B) by first treating the hydrolyzed ethylenevinyl acetate copolymer with a polyfunctional reagent having at least two functional groups capable of reacting with a hydroxy group and amino group and then treating the copolymer with a polyamine, said polyfunctional reagent being selected from the group consisting of a polyisocyanate, a polyepoxide, a polycarboxylic acid anhydride, a polyaldehyde and a polyacid chloride.

9. The process of claim 8, wherein the reactive functional group is an isocyanate group and the polyfunctional reagent is a polyisocyanate.

10. The process of claim 8, wherein the reactive functional group is an epoxy group and the polyfunctional reagent is a polyepoxide.

11. The process of claim 8, wherein the reactive functional group is a carboxylic acid anhydride group and the polyfunctional reagent is a polycarboxylic acid anhydride.

12. The process of claim 8, wherein the reactive functional group is a formyl group and the polyfunctional reagent is a polyaldehyde.

13. The process of claim 8, wherein the reactive functional group is an acid chloride group and the polyfunctional reagent is a polyacid chloride.

14. An antithrombogenic hydrolyzed ethylenevinyl acetate copolymer article, comprising:

a shaped article of a water-insoluble hydrolyzed ethylene-vinyl acetate copolymer containing about 3 to 45 weight % vinyl acetate and about 97 to 55 weight % ethylene, to the surface of which is fixed a fibrinolytic enzyme, wherein the hydrolyzed ethylene-vinyl acetate copolymer contains a reactive functional group capable of forming a covalent bond with said fibrinolytic enzyme and said enzyme is fixed to the polymer through covalent bonding, said reactive functional group being selected from the group consisting of:

(A) an isocyanate group which has been introduced thereinto by treating the hydrolyzed ethylene-vinyl acetate copolymer with a polyisocyanate, (B) an epoxy group which has been introduced thereinto by treating the hydrolyzed ethylene-vinyl acetate copolymer with a polyepoxide, (C) a formyl group which has been introduced thereinto by treating the hydrolyzed ethylene-vinyl acetate copolymer with a polyaldehyde, (D) an acid chloride group which has been introduced thereinto by treating the hydrolyzed ethylene-vinyl acetate copolymer with an acid chloride, (E) a carboxylic acid anhydride group which has been introduced thereinto by treating the hydrolyzed ethylene-vinyl acetate copolymer with a polycarboxylic acid anhydride, (F) an amino group which has been introduced thereinto by treating the hydrolyzed ethylene-vinyl acetate copolymer with an amino acetal, and (G) an amino group which has been introduced thereinto by first treating the hydrolyzed ethylene-vinyl acetate copolymer with a polyfunctional reagent having at least two functional groups capable of reacting with both a hydroxy group and amino group and then treating the copolymer with a polyamine, said polyfunctional reagent being selected from the group consisting of a polyisocyanate, a polyepoxide, a polycarboxylic acid anhydride, a polyaldehyde and a polyacid chloride.

15. The article of claim 14, wherein said article is a tube.

16. The article of claim 15, wherein said tube is a surgical drain.

17. The article of claim 15, wherein said tube is an intravenous catheter.

18. The article of claim 14 wherein said shaped article is formed by extrusion molding.

19. The article of claim 14 wherein said article is suitable for surgical use.

20. The article of claims 14, 15, 16, 17, 18 or 19, wherein said fibrinolytic enzyme is urokinase.

21. The article of claim 14 wherein a functional group having an affinity for substances in the blood which inhibit fibrinolytic enzymes is present in the polymer or hydrolyzate.

22. The article of claim 21 wherein said group is a nitrophthaloyl group.

23. A water-insoluble hydrolyzed ethylene-vinyl acetate copolymer containing about 3 to 45 weight % vinyl acetate and about 97 to 55 weight % ethylene having an antithrombogenic property, comprising:

a water-insoluble hydrolyzed ethylene-vinyl acetate copolymer containing about 3 to 45 weight % vinyl acetate and about 97 to 55 weight % ethylene having fixed thereto a fibrinolytic enzyme, wherein the water-insoluble hydrolyzed ethylene-vinyl acetate copolymer contains a reactive functional group capable of forming a covalent bond with said fibrinolytic enzyme and said enzyme is fixed to said copolymer through covalent bonding, and said reactive functional group being selected from the group consisting of an isocyanate group, an epoxy group, a formyl group, an acid chloride group, a carboxylic acid anhydride group and the reactive functional group having been introduced thereinto by treating the hydrolyzed ethylene-vinyl acetate copolymer having an amino group with a polyfunctional reagent selected from the group consisting of a polyisocyanate, a polyepoxide, a polyaldehyde, a polyacid chloride and a polycarboxylic acid anhydride, having at least two of the reactive functional groups capable of reacting with an amino group, and the fibrinolytic enzyme is fixed to the polymer through covalent bonding, wherein said amino group has been introduced:

(A) by treating the hydrolyzed ethylene-vinyl acetate copolymer with an amino acetal; or (B) by first treating the hydrolyzed ethylene-vinyl acetate copolymer with a polyfunctional reagent having at least two functional groups capable of reacting with a hydroxy group and amino group and then treating the copolymer with a polyamine, said polyfunctional reagent being selected from the group consisting of a polyisocyanate, a polyepoxide, a polycarboxylic acid anhydride, a polyaldehyde and a polyacid chloride.

24. A water-insoluble hydrolyzed ethylene-vinyl acetate copolymer of claim 23, wherein said enzyme is urokinase.

25. A water-insoluble hydrolyzed ethylene-vinyl acetate copolymer of claim 23, wherein said enzyme is streptokinase.

26. A water-insoluble hydrolyzed ethylene-vinyl acetate copolymer of claim 23, wherein said enzyme is plasmin.

27. A water-insoluble hydrolyzed ethylene-vinyl acetate copolymer of claim 23, wherein said enzyme is brinolase.

28. A water-insoluble hydrolyzed ethylene-vinyl acetate copolymer of claim 23 wherein a functional group having an affinity for substances in the blood which inhibit fibrinolytic enzymes is present in the hydrolyzate.

29. A water-insoluble hydrolyzed ethylene-vinyl acetate copolymer of claim 28 wherein said group is a nitrophthaloyl group.

* * * * *